(12) United States Patent
Laghi

(10) Patent No.: US 8,382,852 B2
(45) Date of Patent: Feb. 26, 2013

(54) PROSTHETIC LINER WITH PERSPIRATION ELIMINATION MECHANISM

(75) Inventor: Aldo A. Laghi, Clearwater, FL (US)

(73) Assignee: ALPS Intellectual Property Management, LLC, St. Petersburg, FL (US)

( * ) Notice: Subject to any disclaimer, the term of this patent is extended or adjusted under 35 U.S.C. 154(b) by 0 days.

(21) Appl. No.: 13/167,588

(22) Filed: Jun. 23, 2011

(65) Prior Publication Data

US 2011/0282466 A1    Nov. 17, 2011

Related U.S. Application Data

(63) Continuation-in-part of application No. 12/482,364, filed on Jun. 10, 2009.

(60) Provisional application No. 61/207,876, filed on Jun. 10, 2008.

(51) Int. Cl.
*A61F 2/78* (2006.01)
(52) U.S. Cl. .................................... 623/36
(58) Field of Classification Search ............ 623/36
See application file for complete search history.

(56) References Cited

U.S. PATENT DOCUMENTS

| | | | |
|---|---|---|---|
| 5,192,282 | A | 3/1993 | Draenert |
| 5,376,129 | A | 12/1994 | Faulkner et al. |
| 5,728,168 | A | 3/1998 | Laghi et al. |
| 5,968,047 | A | 10/1999 | Reed |
| 6,454,812 | B1 | 9/2002 | Laghi |
| 6,544,292 | B1 | 4/2003 | Laghi |
| 6,572,655 | B1 | 6/2003 | Johnson |
| 2004/0243251 | A1 | 12/2004 | Carstens |
| 2005/0240283 | A1* | 10/2005 | Kania .................. 623/36 |
| 2007/0032883 | A1 | 2/2007 | Mantelmacher |
| 2007/0168045 | A1 | 7/2007 | Slemker et al. |
| 2010/0070051 | A1 | 3/2010 | Carstens |

\* cited by examiner

*Primary Examiner* — Bruce E Snow
*Assistant Examiner* — Melissa Hoban
(74) *Attorney, Agent, or Firm* — Henry J. Recla

(57) ABSTRACT

A prosthetic elastomeric liner, which can be used without lanyards or straps, in which, upon ambulation, perspiration is voided simultaneously with the reestablishment of a vacuum-aided seal without a vacuum pump. The liner's distal tip comprises a buttress anchored sweat port containing a one way valve continuous with a channel passing through the buttress and liner from its inner surface to its outer surface. The sweat port is connected, optionally integrally, to a prosthetic pin which is inserted into a prosthetic limb.

10 Claims, 6 Drawing Sheets

PROSTHETIC LINER WITH PERSPIRATION ELIMINATION MECHANISM

PRIORITY

This application is a continuation-in-part of U.S. Nonprovisional application Ser. No. 12/482,364 filed on Jun. 10, 2009, which claims priority to U.S. Provisional Application No. 61/207,876, filed on Jun. 10, 2008, which is hereby incorporated by reference.

BACKGROUND

A challenging aspect of treating those who have lost one or more limbs is the restoration of function to the remaining limb (residual limb). Such a restoration often means fitting the residual limb with one or more prostheses, or artificial limbs. A difficulty with artificial limbs is that they often do not physically interface well with the prosthetic patient. For instance, most prostheses comprise a cup, or "socket" into which the residual limb, protected by a sheath or "liner," is inserted and secured. Over the years, the wearing of prosthetics has become more comfortable due to the adoption of prosthetic liners made of synthetic elastomeric and gel materials. Elastomeric liners have the ability to interface between the skin of the wearer and the hard plastic orthotic socket because they have elastic properties and physical consistencies similar to human tissue and can form a vacuum-aided seal between liner and residual limb. As a result, slipping and buckling with ambulation, a problem with earlier liner types, can be reduced. Such liners are indicated in U.S. Pat. Nos. 5,549,709; 6,645,253; 6,761,742; 6,554,868; 6,726,726; 6,926,742 and 6,974,484.

Current gel liner designs available to amputees are generally simple. Many are based upon a single-layer elastomeric sleeve, usually with a slight taper from the open end to a blunted closed end. Because of such simplicity of design, the liners can be manufactured in large numbers from easily worked materials at a relatively low cost.

A problem with elastomerics is their ability to thermally insulate, which tends to increase the rate at which the residual limb perspires. The supple elasticity which makes elastomeric liners suitable for long term skin contact can have negative consequences when the contact with the skin is broken by a liquid, such as perspiration. While mild perspiration may enhance the seal between the residual limb and the liner, the amount produced quickly increases such that a layer of perspiration is formed between the liner surface and the residual limb surface.

Because of the pressures exerted on the liner during ambulation, particularly by the prosthetic socket, the liner can pull away from the residual limb, causing air to be sucked into the liner. As the air pockets join upon further ambulation, a volume is produced between the liner and the limb. The air in the volume contracts and expands with each step, creating a suction and causing the residual limb to expand inside the liner. Such an expansion affects the fit of the limb and liner inside the socket. Many methods for fitting the limb inside the prosthetic socket can require that the limb be repositioned in order to give a comfortable fit. However, upon cessation of ambulation, such as while sitting down or sleeping, it is not uncommon for the residual limb to shrink inside the liner to its original size, necessitating yet another refitting. Thus, it is of paramount importance that air be excluded from the liner. Toward that end, it is thus important that the build-up of perspiration be prevented, and that perspiration be removed as it is being formed, or soon thereafter, from between the liner and the residual limb.

Methods of attaching the liner-covered residual limb into the orthotic socket figure significantly in the sliding caused by perspiration. For example, the use of lanyard type attachments, such as, for example, those used in Mantelmacher et al., U.S. Patent Application Publication No. 2007/0032883, attach and secure the liner at points well above its distal tip. Perspiration, which is emitted over the entire surface of the residual limb, tends to gravitate toward the distal tip of the liner, rather than at points higher in the liner. Thus, while perspiration can cause sliding at any place on the liner/skin interface, sliding is prevalent at the distal tip. In order to surmount the difficulties associated with sliding at the distal tip, lanyard systems or similar methods have been developed which attempt to immobilize the liner through the application of radial and circumferential forces by straps or lanyards at liner points above the distal tip. With lanyard or other methods which apply force at ulterior points of the liner, a residual limb/liner can be effectively immobilized in a prosthetic socket. However, such systems can interfere with the comfort of wearing an elastomeric liner. Furthermore, in the absence of a means for evacuating perspiration from the liner, perspiration can accumulate to such a degree that much of the residual limb/liner interface is affected by perspiration and sliding can occur, despite the presence of the securing means. In such a situation, the securing means can result in chafing or other skin breakdown which can interfere with the ability to continuously wear the liner for long periods of time. Means of perspiration removal which have been used include vacuum ports or nipples to which a vacuum device is permanently or intermittently attached. Such ports are generally located near the distal tip. The ports can limit the ability of some patients to wear a liner for long periods as the nipple can result in constant pressure through the liner on the residual limb at the site of the nipple, which wearers can find to be unbearable over time.

Another means of attaching a liner-covered residual limb to a prosthetic device involves an attachment pin or spike which protrudes from the distal tip of the liner and inserts into a hole in the prosthetic which opens into the socket. The pin is usually supported by a disc or support which is significantly harder and less elastomeric than the liner material. The support can be completely or partially embedded within the distal tip of the liner. It is generally large, even to the point of occupying most of the distal tip. The support is generally large enough to give adequate support to the pin, such that the need for other liner support is minimized. The large support size also spreads the pressure experienced by the distal tip during standing and ambulation over a larger area such that patient discomfort is minimized. The pin generally has ridges or grooves such that it can be releasably held by the prosthetic.

The connection of the elastomeric liner to the prosthetic socket by pin has associated drawbacks, particularly if the pin is the sole means of connection. For instance, upon the distal accumulation of perspiration, the distal tip of the liner can be prone to pulling away from the residual limb, causing sucking and pistoning which can be even worse than that experienced with lanyard methods due to the immobilization of the distal tip of the liner by the pin attachment. In the absence of other means of attachment, the stability of the limb can be compromised.

A prosthetic liner having the stability associated with a distal tip pin, but without the same susceptibility to performance deterioration due to perspiration build up would represent a welcome advance in the art.

BRIEF SUMMARY OF THE INVENTION

It is an object of the present invention to provide a liner in which a vacuum is self-establishing upon ambulation. It is a further object of the present invention to provide a prosthetic liner having a perspiration voiding system which functions upon ambulation without a vacuum pump. It is an object of the present invention to provide a comfortable prosthetic liner which securely locks into a prosthetic and bears an everted sweat port, yet permits ambulation without pain.

The present invention is a pin locking prosthetic liner apparatus having reduced air breach and associated pistoning. The apparatus does not require the use of lanyards or securing means at points other than the spike in the distal tip region. The apparatus comprises a liner body, a buttress section, a sweat port comprising a one-way valve; at least one channel through the liner body continuous with the sweat port, a pin, optionally integral with the sweat port, and, optionally, an inner fabric lining which does not come closer than a perpendicular distance of 0.5 inches from the proximal edge of the liner. By "perpendicular distance" it is meant the distance is measured along a projection of the vertical axis onto the liner.

BRIEF DESCRIPTION OF THE DRAWINGS

FIG. 5B—A side view of a separate sweat port (4''') having vent (8") and duck bill valve (9).

FIG. 6A—A perspective view of the sweat port (4" or 4''') and pin (14) combination having vent (15) extending axially through the pin.

FIG. 6B—A perspective view of the sweat port (4" or 4''') and pin (14') combination having vent (16) extending radially from the pin.

DETAILED DESCRIPTION OF THE INVENTION

Figure 1:
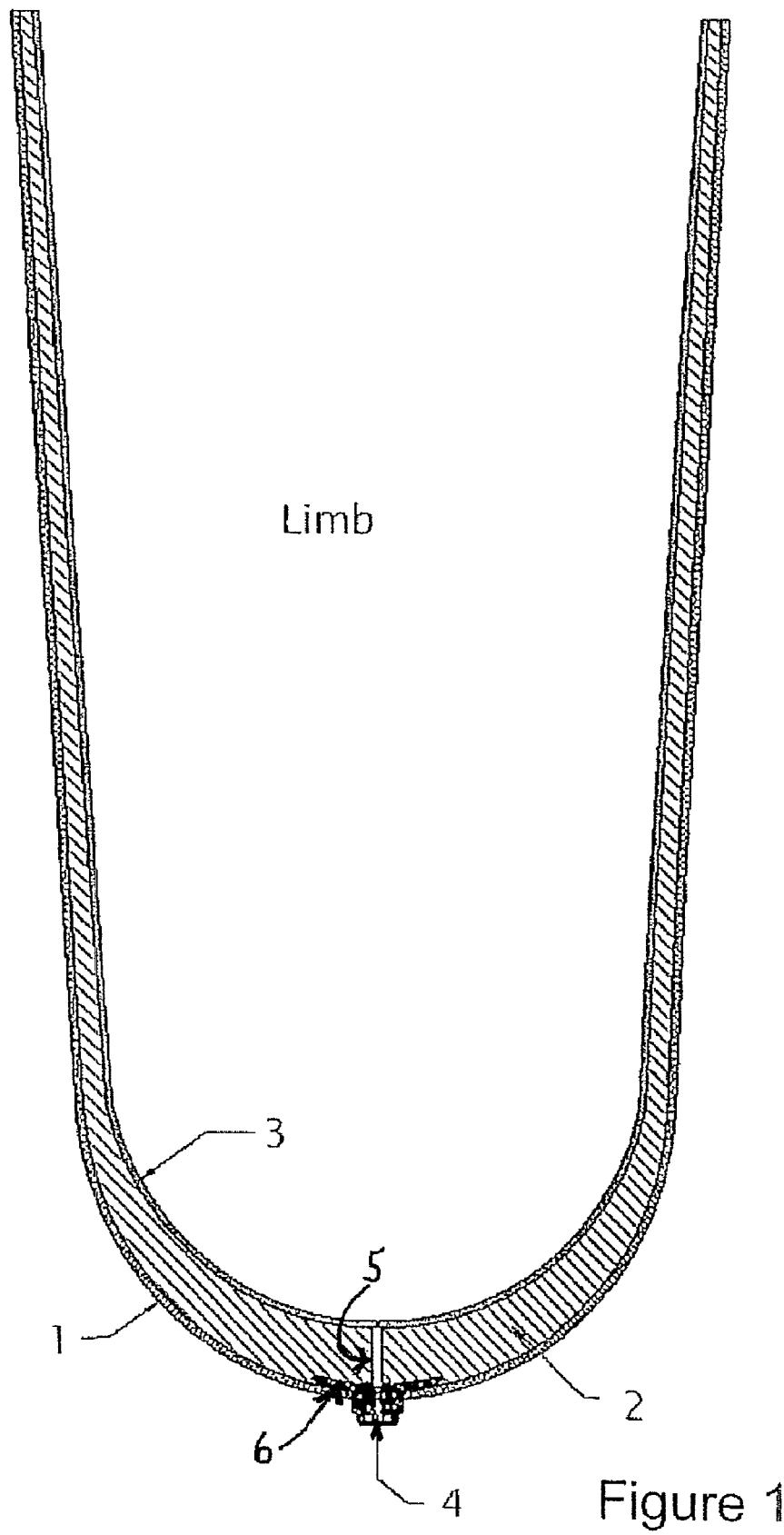
FIG. 1—A cross-section of a first embodiment of the present invention comprising an elastomeric liner body (2), a fabric liner (3), an open channel (5), a buttress (6), and a sweatport (4) adapted to contain a duckbill one way valve (not shown). Also shown is a fabric overliner (1).
Figure 2:
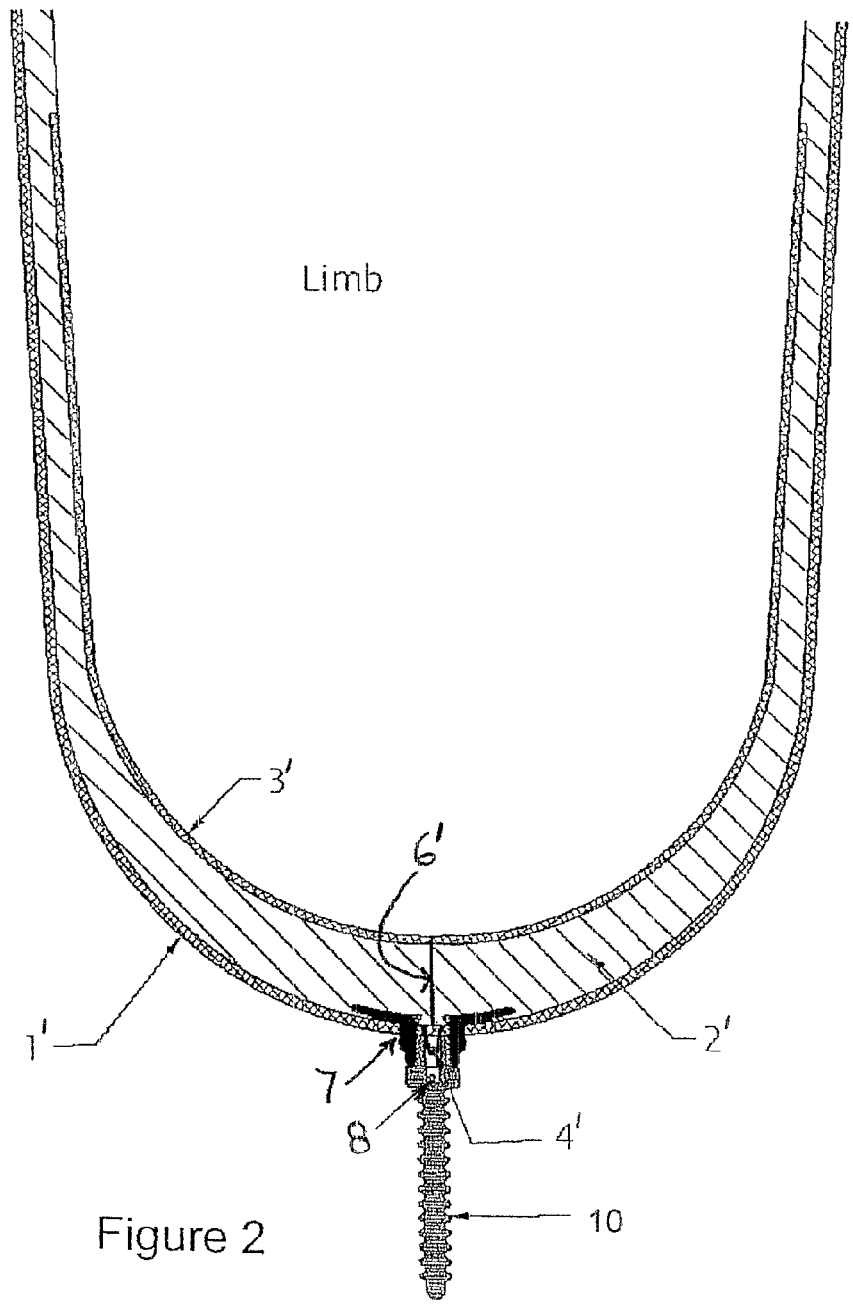
FIG. 2—A cross section of a second embodiment of the present invention comprising an elastomeric liner body (2'), a fabric liner (3'), a closable channel (6'), a buttress having an internally threaded connection (7), a sweat port having external threads (4'), vent (8) and a one-way valve as more graphically illustrated in FIGS. 5A and 5B, and a pin (10). Also shown is a fabric overliner (1').
Figure 3:
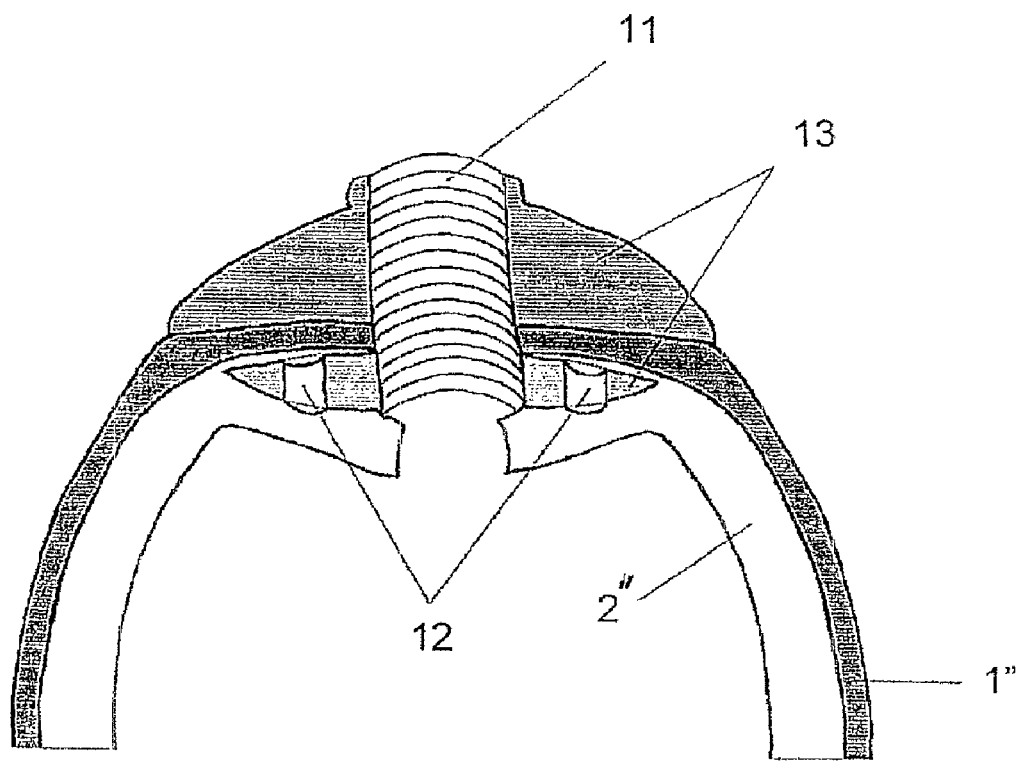
FIG. 3—A cross-section of a third embodiment of the present invention comprising a buttress having two cylindrically symmetric sections (13), an elastomeric liner (2") which has been melt sealed to the inner buttress section, and a threaded channel (11). Note the elastomer of the liner has flowed through holes (12) in the inner buttress section. Also shown is a fabric overliner (1").

The present invention as illustrated in the figures comprises an elastomeric liner comprising an open proximal end having a proximal edge and a closed distal end. The distal end comprises a distal tip. A sweat port (4, 4', 4" and 4''') is positioned at the distal tip. The distal tip comprises, within it or attached to it, a buttress (6, 7 and 13). The buttress generally comprises a polymeric material having a degree of elasticity which is less than that of the liner (2, 2' and 2"), or in other embodiments, the buttress comprises a support material, such as aluminum or other metals; or rigid plastics or other materials, which are over laid with a polymeric material. In embodiments in which the buttress contacts the prosthetic socket, the polymeric component of the buttress softens the contact and prevents grinding which can wear the socket and irritate the wearer. As illustrated in FIGS. 1 and 2, the buttress can be embedded within the liner during liner manufacture, or in other embodiments, it is adhered to the end of the liner. As illustrated in FIG. 3, it is preferably underlain by a section of the liner, regardless of whether it is embedded within the liner during liner manufacture or it is adhered to the liner distal tip during or after manufacture. The buttress generally has cylindrical symmetry about the long axis of the liner. In one embodiment, illustrated in FIGS. 1 and 2, it is a disc of a thickness less than liner thickness and is entirely embedded within the liner. In another embodiment, illustrated in FIG. 3, it is partially within the liner and partially outside the liner ("anchored" in the liner). This embodiment is particularly useful in situations where a large buttress which is thicker than the liner is required. The buttresses (6, 7 or 13) each include a cylindrical extension having a bore therethrough for receiving a sweat port (4, 4', 4" and 4''').

In the embodiment illustrated in FIG. 3, the buttress is of a form such that a distal tip portion of the liner elastomer is between sections (13) of buttress having cylindrical symmetry. One of the buttress sections is embedded in the distal tip of the liner, and another buttress section is externally attached to the elastomeric liner distal tip. Such an arrangement can be created by mechanically sealing a portion of the distal tip section between the two buttress components, or it can be achieved by casting the liner around the buttress components, or otherwise including the buttress components in the fabrication and cooling of the liner, such that the buttress sections are essentially melt-sealed on both the inside and the outside of the distal tip of the liner.

When the liner is in use, the buttress is structurally sandwiched between the residual limb stump and the socket, providing critical support for the pin (discussed infra). In some embodiments, the support is further improved in that the buttress is shaped to facilitate insertion into the socket, or the socket has a shape which complements the shape of the buttress. In preferred embodiments, the buttress extends at least 0.5 cm from the vertical axis of the liner, and is at least half the thickness of the liner body at its distal tip, and preferably, at least as thick as the liner body at its distal tip.

The liner body which can be used in the system of the present invention comprises an elastomeric material preferably of a type compatible with long periods of dynamic wearer contact. Such materials are known in art and may include the following polymer types and materials which include them: polyurethanes; block copolymers such as styrene block copolymers, generally non-limiting examples of which may include SEBS, SEPS, SEEBS and SEEPS and other types of styrene block copolymers. Further examples of styrene block copolymers which may be useful in the liner of the present invention include the so-called "controlled distribution" polymers, such as those disclosed in U.S. Pat. No. 7,226,484; United States Patent Application Publication Nos. 20070238835; 20050008669. Other potentially useful polymers may include so-called "crystalline" polymers, such as, for example, polymers disclosed in U.S. Pat. Nos. 5,953,396; 6,420,475; and 6,148,830. The above list is non-limiting, and in general, the list of acceptable polymers and gels includes those known in the art to be useful in the fabrication of prosthetic liners. By the term "gel," it is meant a polymer having means associated with it, through means known in the art, such as absorption, mixing or other, a plasticizer. A suitable liner which can be modified to include a buttress is the "EZ Gel" liner, available from Alps South L.L.C.

As illustrated in FIGS. 1-3, the liner body comprises a channel (5, 6' and 11) passing through the liner from its inner surface to its outer surface. The channel (6') may be formed by piercing or punching, with or without the removal of elastomeric material from the liner. As illustrated in the embodiment of FIG. 2, the liner is pierced such that little or no material is displaced, and the channel (6') is essentially closed by the elastomeric response of the liner material. In such cases, the pressures associated with the ambulatory motion of the patient can cause perspiration produced during wear to be squeezed through the channel. The channel (6') essentially acts as a relief valve which allows the elimination of perspiration emitted by the wearer. The perspiration occupies a volume between the liner and the wearer, potentially giving rise to undesirable interruption of vacuum. In the foregoing embodiment, a closed channel can assist in maintaining and re-establishing the vacuum.

As illustrated in FIGS. 1 and 3, the channel (5 and 11) can also be open. Such a situation is experienced with removal or displacement of liner material, such as with a punch or heated awl-type tool. As the buttress sections extend over the distal tip, the channel traverses them such that it opens out onto the distal tip i.e., the portions of the channel traversing the elastomer and those traversing the buttress sections are continuous. It should be noted that the channels through the elastomer and those through the buttress sections need not be of the same diameter. For example, it is permissible for the channel through the elastomer to be of the type described above in which perspiration can be passed under pressure.

The distal tip of the liner, including the buttress, comprises a sweat port (4, 4', 4" and 4'"). The sweat port is continuous with the channel, and it is preferably located approximately at the distal apex. By "distal apex" it is meant the lowest point on the long axis of the liner, including the buttress, when its long axis is oriented vertically with its distal tip pointing downward. As explained in greater detail infra, the sweat port is attached to a pin (10, 14 and 14') which is received by the socket of the prosthetic. In some embodiments, the pin may not be precisely at the distal tip. For example, it may be desirable in some embodiments to attach the prosthetic in such a way that the pin is located at a point near, but not precisely at the distal apex. However, it should be noted that regardless of where the sweat port is located, it is continuous with the channel through the liner. The sweat port is a nipple or port extending from or partially/fully embedded or recessed in the distal tip of the liner. In a preferred embodiment, at least a portion of the bore through the cylindrical extension of the buttress is threaded, and the sweat port comprises matching threads by which it can be screwably attached to the extension.

The sweat port contains a one-way valve (9) which allows an exit for perspiration, air, and other liquids or gases which cause a volume increase between the liner and the wearer. The valve is small enough to fit within the sweat port and can be one of many different kinds of check valves. In different embodiments, the valve is a duckbill, ball, diaphragm, swing, clapper, lift or other type of check valve. In a preferred embodiment, the one way valve is a duck bill valve.

The sweat port is attached to a pin which, in use, is inserted into a prosthetic limb. The pin is a spike of a durable material such as aluminum or other metal, which is generally in the range of from about 1.5 to about 3 inches, which is inserted into a prosthetic limb. It can bear protrusions or other irregularities in profile which aid in securely fitting the prosthetic to the liner. Optionally, the prosthetic limb can include a locking mechanism which maintains the prosthetic securely in place.

Figure 4:
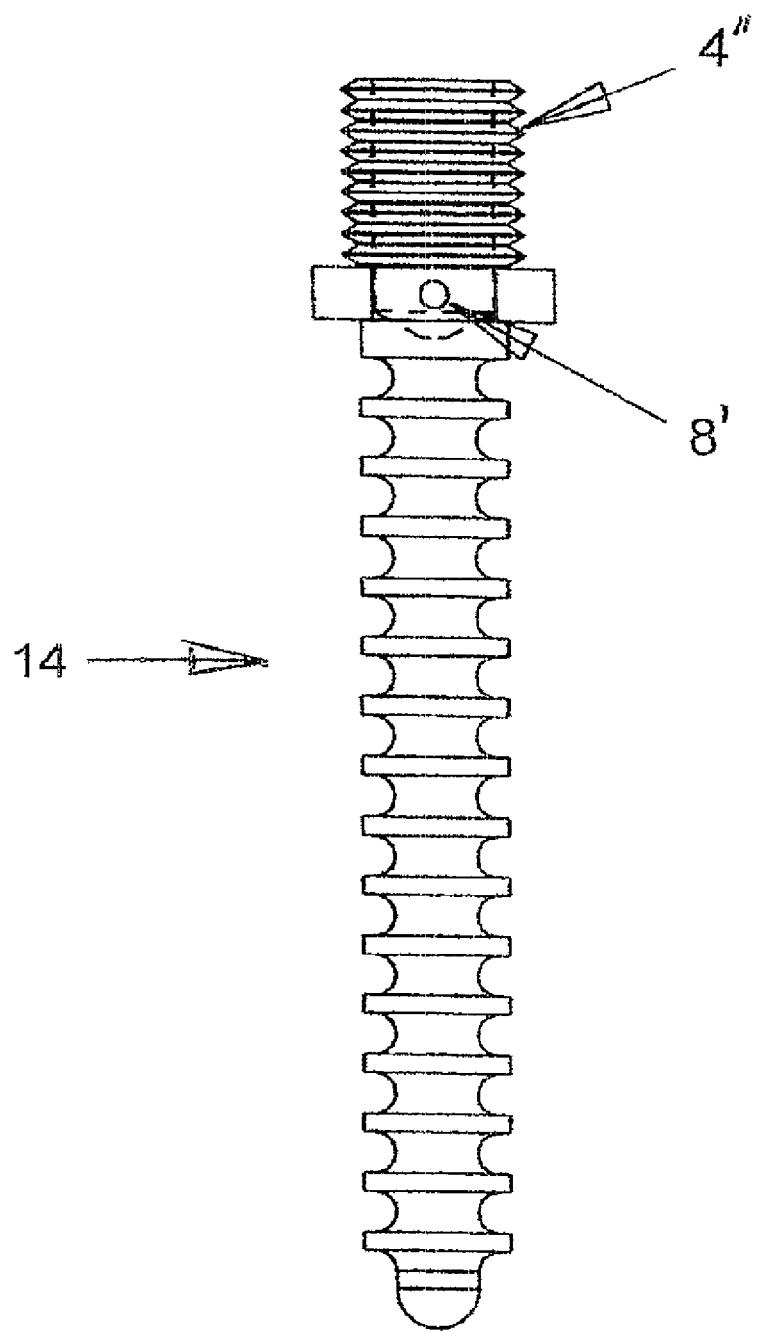
FIG. 4—A perspective view of an integral sweat port and pin combination comprising a pin (14) and a sweat port (4") having a vent (8') extending from the sweat port.
Figure 5A:
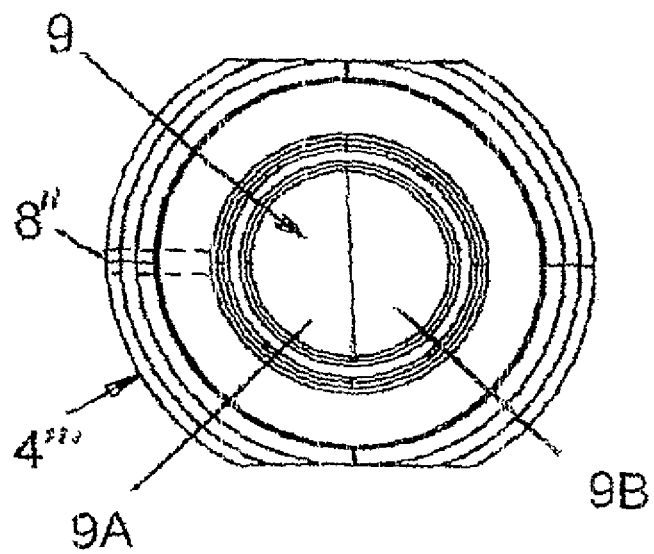
FIG. 5A—A top view of a separate sweat port (4''') having vent (8") and duck bill valve (9) with flaps 9A and 9B.
Figure 5B:
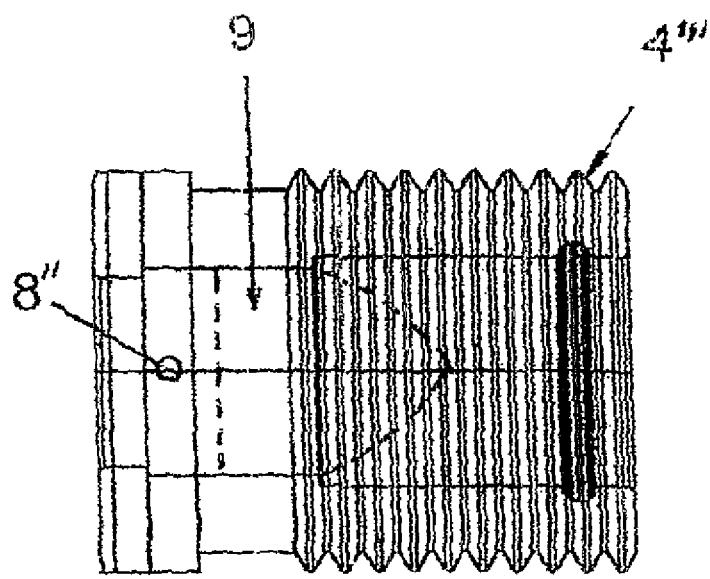
Figures 6A, 6B:
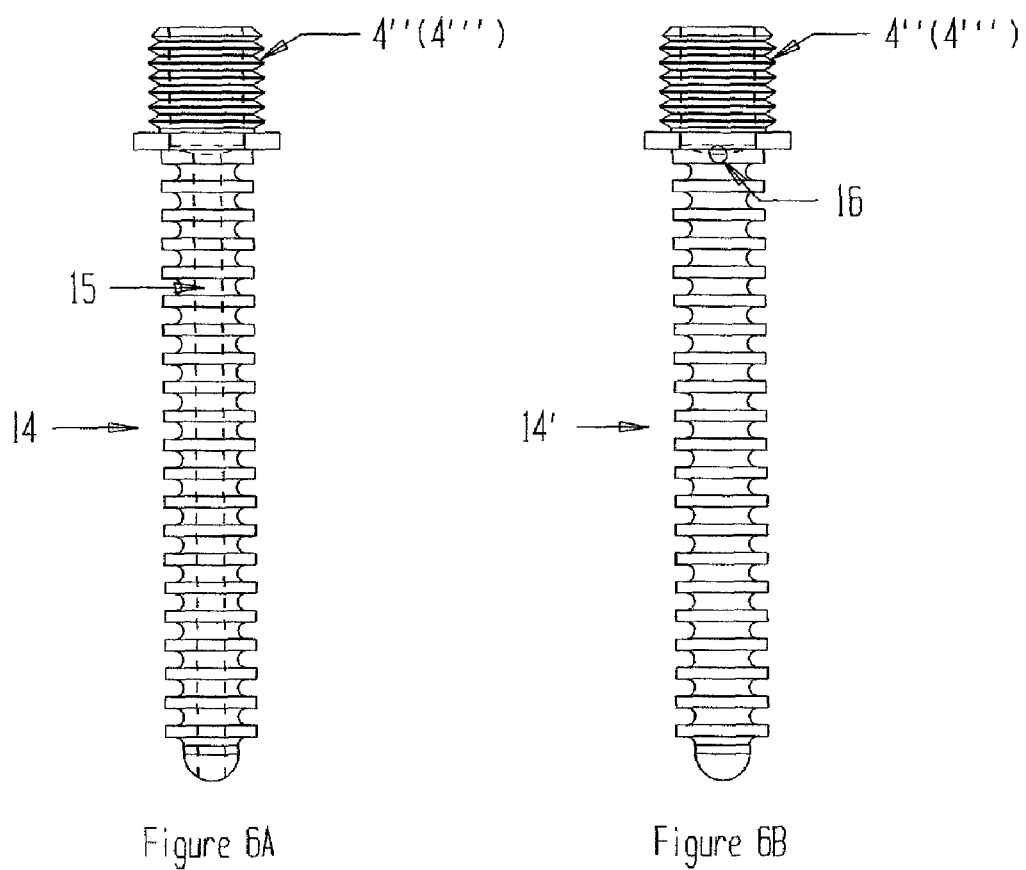

The sweat port can be removably attached in series with the pin as illustrated in FIG. 2 to form a port/pin assembly. Such a connection can be a threaded connection or other method of sealably engaging the port and the pin and generally includes a vent for the efflux of perspiration or another means of dissipating and draining the perspiration passing from the interior of the liner. In a preferred embodiment of the present invention, the sweat port is integral with the pin, depicted in FIG. 4, for example, where a vent is clearly visible on the side of the assembly.

In a preferred embodiment of the present invention, the liner body (2, 2' and 2") has a fabric liner (3 and 3') on its inner surface which over lays the distal tip, and in some embodiments extends along the inner surface a distance in the range of from about 1 to about 19 inches from the proximal edge of the liner. In some embodiments, the fabric liner extends to within no less than 0.5 inches from the proximal edge of the liner, and in other embodiments, to within no less than 1.0 inches from the proximal edge. A fabric which absorbs perspiration helps to wick it toward the distal end of the liner. Preferred fabrics are those that absorb emitted perspiration, such as natural fibers, such as, for example, felt, wool and cotton fabrics and materials, as well as synthetic fabrics and materials, such as, for example rayon, orlon and nylon. In other embodiments, a sock which has high perspiration absorbency can function as the fabric liner, preferably extending to no less than 0.5 inches from the proximal edge. It is preferred that the fabric have a thickness in the range of from about 0.5 to about 3.0 millimeters. It should be noted that regardless of fabric type and thickness, the present invention includes within its ambit embodiments comprising fabrics or materials having the ability to wick and/or store perspiration such that when weight is placed on the limb, the residual limb compresses the perspiration bearing fabric or material, and some or all of the perspiration is forced through the channel and the sweat port.

Furthermore, the fabric liner can be an elastic fabric to facilitate its ability to stretch somewhat with the motion of the liner. In some embodiments, the fabric liner comprises fabrics which are manufactured in such a way to optimize their elastic properties, especially when used as a liner material for an elastomeric liner body.

A benefit of the present invention is that the constant elimination of perspiration through the sweat port one-way valve aids in restoring a vacuum to the liner/residual limb complex. A further benefit is that as small amounts of sweat are constantly eliminated through the sweat port, they evaporate readily from the area surrounding the sweat port, and thus no need exists to dispose of larger amounts of perspiration. However, if desired, perspiration can be routed to a receptacle, such as a void in the prosthetic or another method of containment.

In general, even in the absence of fabric, the compression motion which occurs during ambulation acts to force accumulated perspiration through the channel into the sweat port, and ultimately through the one-way valve. In this way, emitted perspiration is voided before it can have a significant effect on the vacuum, which is renewed with each step.

In general, liners of the present invention may comprise an elastic or elastomeric fabric which overlays all or a portion of the outer surface of the liner body. Such fabrics can have an elasticity which is greater than or less than the elasticity of the liner body. In some embodiments of the present invention, the liner comprises elastic or elastomeric fabrics to improve the fit of the liner and affect the overall elasticity of the liner.

It should be noted that the pin of the present invention can be used with both trans-femoral and trans-tibial amputees. It could be expected that in order to tailor the effectiveness of the inventive liner product and method to a particular circumstance, it may be expedient for one of skill in the art to locate the sweat port/pin at a location other than the distal apex in order to facilitate an efficient evacuation of perspiration. In general, because of the physical parameters involved in ambulation, it is expected that the location of the sweat port would not be more than an inch from the distal apex, and in all likelihood, a smaller distance. A liner having a sweat port which is relocated to meet the perspiration drainage needs of a particular wearer does not represent a departure from the teachings herein and is encompassed within the scope of the present invention.

We claim:

1. A liner comprising:
   a) an elastomeric liner body comprising an open proximal end and a closed distal end except for a centrally extending channel, said liner body defining an interior volume;
   b) at least one symmetrical buttress element mounted centrally to said distal end of said liner body and having a cylindrical member extending away from said distal end of said liner body; said cylindrical member defining a bore therethrough having an inlet end and an outlet end;
   c) said channel in the distal end of the liner body having an inlet in fluid communication with said interior volume of said liner body and an outlet in fluid communication with said inlet end of said cylindrical member;
   d) a sweat port mounted in said outlet end of said bore of said cylindrical member and defining a passageway therethrough in fluid communication with said channel, said sweat port having a one-way valve mounted in said passageway and adapted to provide one-way flow from said interior volume;
   e) a pin attached to said sweat port downstream of said one-way valve, said pin extending axially with respect to said liner body for securely fitting said liner to a prosthetic limb; and
   f) a vent extending through said pin and terminating in a vent port, said vent extending axially or radially through said pin to said vent port and fluidly communicating said passageway of said sweat port to the surrounding environment.

2. A liner as in claim 1, wherein said liner additionally comprises a fabric liner or pad which does not extend to the proximal edge of the liner body.

3. A liner as in claim 2, wherein said fabric liner extends to no less than one inch from the proximal edge of the liner body.

4. A liner as in claim 1, wherein a section of said at least one buttress element is completely embedded within the liner body.

5. A liner as in claim 1, wherein a section of said at least one buttress element is attached to the exterior of said distal end of said liner body.

6. A liner as in claim 1, wherein said one-way valve is a duckbill valve.

7. A liner as in claim 1, wherein said channel is a self-closable channel formed in said elastomeric liner body.

8. A liner as in claim 1, wherein said sweat port and said pin are integral.

9. A liner as in claim 1, wherein the sweat port and pin are releasably attached.

10. A liner as in claim 1, wherein the sweat port and pin are attached via a threaded connection.

* * * * *